United States Patent [19]

Juby

[11] 4,192,944

[45] Mar. 11, 1980

[54] OPTIONALLY SUBSTITUTED 4-OXO-4H-PYRIDO[1,2-A]PYRIMIDINE-3-N-(1H-TETRAZOL-4-YL)CARBOXAMIDES AND THEIR USE AS ANTIALLERGY AGENTS

[75] Inventor: Peter F. Juby, Jamesville, N.Y.

[73] Assignee: Bristol-Myers Company, New York, N.Y.

[21] Appl. No.: 892,714

[22] Filed: Apr. 3, 1978

[51] Int. Cl.$^2$ .................. C07D 403/12; A61K 31/505
[52] U.S. Cl. ........................... 544/282; 544/119; 544/250; 544/252; 124/251; 546/304; 546/311
[58] Field of Search ............... 544/250, 252, 282, 119

[56] References Cited

U.S. PATENT DOCUMENTS

| | | | |
|---|---|---|---|
| 3,072,485 | 1/1963 | Reynolds et al. | 544/282 |
| 3,585,198 | 6/1971 | Meszaros et al. | 544/282 |
| 3,929,787 | 12/1975 | Yale | 424/251 |
| 3,960,847 | 6/1976 | Yale | 424/251 |
| 4,017,625 | 4/1977 | Kadin | 544/252 |

OTHER PUBLICATIONS

Cox et al., "Adv. in Drug Res.", vol. 5, 1970, pp. 115–196.
Landquist "J. Chem. Soc.", (C), 1971, pp. 2735–2738.
Okamoto et al., "Chem. and Pharm. Bul.", vol. 22, No. 2, 1974, pp. 243–247.
Adams et al., "J. Amer. Chem. Soc.", vol. 74, 1952, pp. 5491–5497.
Shur et al., "J. Org. Chem.", vol. 33, No. 8, 1968, pp. 3015–3020.
Meszaros et al., "Arzneim.-Forsch.", vol. 22, No. 5, 1972, pp. 815–829.
Meszaros et al., "Tetrahedron Letters", No. 12, 1975, pp. 1019–1020.

*Primary Examiner*—Alton D. Rollins
*Assistant Examiner*—James H. Turnipseed
*Attorney, Agent, or Firm*—David M. Morse

[57] ABSTRACT

A novel series of optionally substituted 4-oxo-4H-pyrido[1,2-a]pyrimidine-3-N-(1H-tetrazol-5-yl)carboxamides is provided for use as inhibitors of allergic reactions. The compounds exhibit antiallergy activity by both oral and parenteral routes of administration.

27 Claims, No Drawings

OPTIONALLY SUBSTITUTED 4-OXO-4H-PYRIDO[1,3-a]PYRIMIDINE-3-N-(1H-TETRAZOL-4-YL)CARBOXAMIDES AND THEIR USE AS ANTIALLERGY AGENTS

BACKGROUND OF THE INVENTION

1. Field of the Invention

This invention relates to optionally substituted 4-oxo-4H-pyrido[1,2-a]pyrimidine-3-N-(1H-tetrazol-5-yl)carboxamide derivatives and to their use as inhibitors of allergic reactions.

2. Description of the Prior Art

Various medicinal agents have been employed in the treatment of allergic reactions such as bronchial asthma and allergic rhinitis which are believed to result mainly from antigen-antibody interaction. With respect to bronchial asthma, one of the most serious of these allergically-mediated diseases, bronchodilators such as theophylline, isoproterenol, epinephrine and atropine are used primarily in providing symptomatic relief. These agents, however, have undesirable side effects, e.g. cardiac stimulation and gastrointestinal distress.

With the recent introduction of disodium cromoglycate described by J. S. G. Cox, et al. in *Adv. in Drug Res.*, 5, 115–196 (1970), the physician has been provided with an agent which, when administered to asthmatic patients prior to inhalation of specific antigens, inhibits the release of mediators, e.g. histamine and SRS-A (slow-reacting-substance of anaphylaxis), believed to be responsible for the asthmatic response. While making possible a prophylactic treatment for bronchial asthma without cardiovascular side effects and thus representing a significant advance, disodium cromoglycate suffers from a major disadvantage in that it is not orally absorbed and must be administered by inhalation.

With respect to the compounds of the present invention, no examples of 4-oxo-4H-pyrido[1,2-a]pyrimidine-3-N-(1H-tetrazol-5-yl)carboxamides have been found in the literature. Numerous examples of the pyrido[1,2-a]pyrimidine ring system, however, are known, including many oxo derivatives.

U.S. Pat. No. 3,585,198 reviews some of the literature of the pyrido[1,2-a]pyrimidines and discloses compounds of the general formula

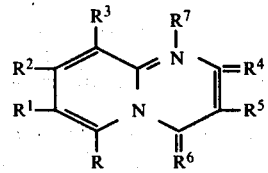

where R, $R^1$, $R^2$ and $R^3$ may be hydrogen, alkyl, alkoxy, halogen, nitro or amino, $R^4$ is hydrogen, alkyl, aralkyl, aryl, =O, alkoxy, halogen or hydroxy, $R^5$ is hydrogen, halogen, a —CH$_2$—OH group, a carboxylic acid or carboxylic acid derivative group, $R^6$ is hydrogen, alkyl, aralkyl, aryl, =O, alkoxy, halogen or hydroxy and $R^7$ is hydrogen, alkyl, aryl, or alkyl. The disclosed compounds are said to exhibit analgesic, antipyretic and narcosis potentiating effects.

U.S. Patent 3,929,787 discloses 2-aryl-9-alkyl-4H-pyrido[1,2-a]pyrimidin-4-one compounds of the formula

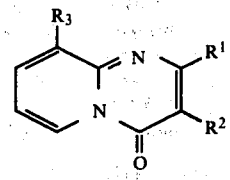

where $R^1$ is phenyl or substituted phenyl, $R^2$ is hydrogen or alkyl and $R^3$ is alkyl. These compounds are reported to be intermediates in preparing the corresponding 6,7,8,9-tetrahydro derivatives which possess central nervous system depressant activity.

U.S. Pat. No. 3,072,485 discloses inter alia compounds of the formula

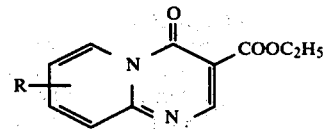

where R is hydrogen, bromo, chloro, iodo or methyl. The compounds are used as photographic sensitizers.

Compounds of the formula

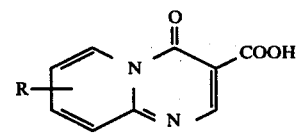

where R is hydrogen, 9-methyl or 8-methyl are disclosed by Okamoto, et al. in Chem. Pharm. Bull. (Tokyo), 22, 243 (1974). No pharmacological utility for the compounds is indicated.

U.S. Pat. No. 3,960,847 discloses inter alia 9-substituted pyrido[1,2-a]pyrimidines of the formula

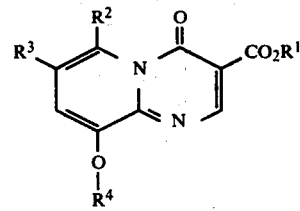

where $R^1$ is hydrogen or C$_1$–C$_4$ alkyl, $R^2$ and $R^3$ are hydrogen, C$_1$–C$_4$ alkyl, CF$_3$, F, Cl or Br and $R^4$ is inter alia an alkyl radical substituted by a phenyl or substituted phenyl radical, such as benzyl, substituted benzyl, phenethyl or substituted phenethyl. The compounds are said to have both central nervous system and hypotensive activities.

J. K. Landquist has described in *J. Chem. Soc.* (C), 2735 (1971) the preparation of the carboxamide compound of the formula

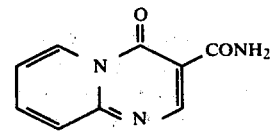

by treatment of the corresponding ethyl ester with ammonium hydroxide in ethanol. No pharmacological utility is given for the disclosed carboxamide.

Other references to the chemistry of pyrido[1,2-a]-pyrimidinones include *J. Amer. Chem. Soc.*, 74, 5491 (1952), *J. Org. Chem.*, 33, 3015 (1968), *Arzneim.-Forsch.*, 22, 815 (1972) and *Tetrahedron Lett.*, (12), 1019 (1975).

SUMMARY OF THE INVENTION

This invention relates to new therapeutically useful 4-oxo-4H-pyrido[1,2-a]pyrimidine-3-N-(1H-tetrazol-5-yl)carboxamide derivatives, to processes for their preparation, to pharmaceutical compositions containing them and to methods for treating allergically-mediated diseases in mammals by administration of such derivatives or pharmaceutical compositions.

The compounds of the present invention are useful in the prophylactic treatment of allergic conditions such as bronchial asthma, allergic rhinitis, urticaria, systemic anaphylaxis, conjunctivitis, atopic dermatitis and food allergies. They are of value in both reagin-mediated Type I hypersensitivity asthma (extrinsic asthma) and the so-called intrinsic asthma in which no sensitivity to any extrinsic antigen can be demonstrated.

The antiallergy agents of the present invention may be represented by the formula

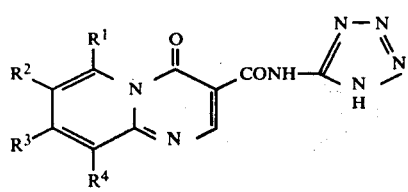

wherein $R^1$, $R^2$, $R^3$ and $R^4$ which may be the same or different are each hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, -O-(lower)alkenyl, —O—$(CH_2)_m$CH$(CH_2)_n$ in which m is 0 or an integer from 1 to 6 and n is an integer from 2 to 7, —OCH$_2$(CH$_2$)$_x$O(CH$_2$)$_y$CH$_3$ in which x and y are each independently O or an integer from 1 to 6, $CF_3$, hydroxy, hydroxymethyl, (lower)alkylthio, amino, nitro, —N$(CH_2)_r$ in which r is 4 or 5,

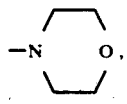

(lower)alkylamino, di(lower)alkylamino, carboxyl, —$CO_2$—(lower)alkyl, phenyl, phenyl substituted by one or two (lower)alkyl, (lower)alkoxy or halogen radicals, benzyl, (lower)alkylsulfinyl, $R^c$-CO- in which $R^c$ is (lower)alkyl, $R^c$-COO- in which $R^c$ is (lower)alkyl, —O(CH$_2$)$_k$OH in which k is an integer from 2 to 6,

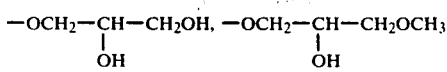

or —OCH$_2$C$_6$H$_5$, or $R^2$ and $R^3$ or $R^3$ and $R^4$ when taken together are methylenedioxy or —(CH$_2$)$_n$— in which n is 3, 4 or 5, and pharmaceutically acceptable salts thereof, with the provisos that (1) no more than two of $R^1$, $R^2$, $R^3$ and $R^4$ are bulky groups, i.e. tertiary alkyl or tertiary alkoxy, and when two of said $R^1$, $R^2$, $R^3$ and $R^4$ are bulky groups, they are located on non-adjacent positions; and (2) no more than two of $R^1$, $R^2$, $R^3$ and $R^4$ may be nitro or trifluoromethyl groups.

The $R^1$, $R^2$, $R^3$ and $R^4$ substituent groups disclosed above may be further defined as follows:

(a) Halogen includes chlorine, bromine, fluorine and iodine;

(b) (Lower)alkyl includes both straight and branched chain saturated aliphatic hydrocarbon radicals having from 1-6 carbon atoms inclusive, e.g. methyl, ethyl, n-propyl, isopropyl, n-butyl, isobutyl, sec-butyl, tert-butyl, n-pentyl, isopentyl, n-hexyl, etc.;

(c) (Lower)alkenyl includes straight or branched unsaturated aliphatic hydrocarbon radicals containing one double bond and having from 2-6 carbon atoms inclusive, e.g. vinyl, allyl, isopropenyl, 2- or 3-methallyl or 3-butenyl;

(d) (Lower)alkoxy includes $C_1$-$C_6$ alkoxy radicals, the alkyl portion of such radicals being defined as in (b) above. Examples include methoxy, ethoxy, n-propoxy, isopropoxy, n-butoxy, isobutoxy, sec-butoxy, n-pentyloxy, isopentyloxy, n-hexyloxy, etc.;

(e) —O—(Lower)alkenyl groups include radicals in which the alkenyl portion is as defined above in (c), e.g. vinyloxy, allyloxy or isopropenyloxy;

(f) —O—$(CH_2)_m$—CH$(CH_2)_n$ includes cyclo(lower)alkyloxy and cyclo(lower)alkyl-($C_1$-$C_6$)alkyloxy groups in which the cycloalkyl ring contains from 3 to 8 carbon atoms, preferably 3-6 carbon atoms. Examples of such groups are cyclopropyloxy, cyclobutyloxy, cyclopentyloxy, cyclohexyloxy, cycloheptyloxy, cyclopropylmethyloxy, cyclopropylethyloxy, cyclobutylmethyloxy, cyclobutylethyloxy, cyclopentylmethyloxy, cyclohexylmethyloxy, cyclohexylethyloxy and cyclohexylpropyloxy;

(g) —O—CH$_2$(CH$_2$)$_x$O(CH$_2$)$_y$CH$_3$ includes radicals such as —OCH$_2$OCH$_3$, —OCH$_2$CH$_2$OCH$_3$, —OCH$_2$C-H$_2$OCH$_2$CH$_3$, —OCH$_2$OCH$_2$CH$_3$ and —OCH$_2$CH$_2$C-H$_2$OCH$_2$CH$_3$;

(h) (Lower)alkylthio includes $C_1$-$C_6$ alkylthio radicals in which the alkyl portion is as defined above in (b). Examples of such groups are methylthio, ethylthio, n-propylthio and n-butylthio;

(i) (Lower)alkylamino includes $C_1$-$C_6$ alkylamino radicals in which alkyl is as defined in (b). Examples of such groups are methylamino, ethylamino, propylamino and butylamino;

(j) Di(lower)alkylamino includes di $C_1$-$C_6$ alkylamino radicals in which alkyl is as defined above in (b). Examples of such groups are dimethylamino and diethylamino;

(k) -$CO_2$-(Lower)alkyl includes ester radicals in which the alkyl moiety is as defined above in (b), e.g. carbomethoxy, carbethoxy, carbopropoxy and carbobutoxy;

(l) (Lower)alkylsulfinyl represents radicals of the formula

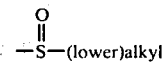

in which the alkyl portion is as defined above in (b). Examples of such radicals include methylsulfinyl, ethylsulfinyl, n-propylsulfinyl, isopropylsulfinyl, n-butylsulfinyl, sec-butylsulfinyl, isobutylsulfinyl, t-butylsulfinyl, n-pentylsulfinyl and n-hexylsulfinyl. The most preferred alkylsulfinyl group is methylsulfinyl;

(m) $-N(CH_2)_r$ includes pyrrolidino and piperidino;

(n) Cyclo(lower)alkyl means cycloalkyl radicals having from 3–6 carbon atoms. Examples include cyclopropyl, cyclobutyl, cyclohexyl, etc.;

(o) $R^2$ and $R^3$ or $R^3$ and $R^4$ taken together may be $(CH_2)_n$ which represents a saturated five, six or seven membered monocyclic hydrocarbon radical fused to the A ring of the pyrido[1,2-a]pyrimidine ring system, e.g.

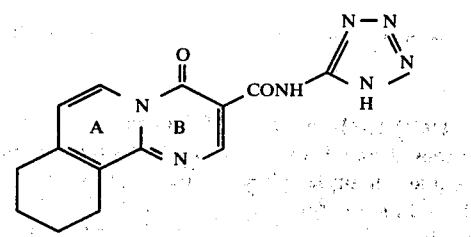

n = 4 or

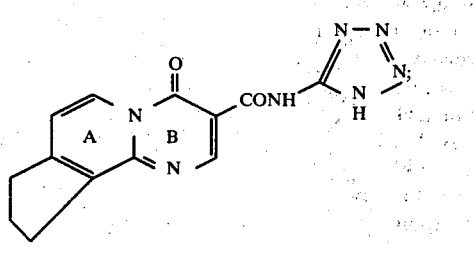

n = 3

(p) (Lower)alkynyl represents straight or branched unsaturated aliphatic hydrocarbon radicals containing one triple bond and having from 2 to 6 carbon atoms inclusive, e.g. ethynyl, propargyl, butynyl, pentynyl or hexynyl;

(q) (Lower)alkoxy(lower)alkyl represents radicals where the (lower)alkoxy and (lower)alkyl portions are as defined above in (d) and (b), respectively, e.g. methoxymethyl, methoxyethyl, ethoxymethyl, ethoxyethyl, methoxypropyl, etc.; and (r) Cyclo(lower)alkyl(lower)alkyl represents radicals in which the cyclo(lower)alkyl and (lower)alkyl portions are as defined above in (n) and (b) respectively, e.g. cyclopropylmethyl, cyclopropylethyl, cyclopropylbutyl, cyclohexylmethyl, cyclohexylethyl, etc.

DETAILED DESCRIPTION

A preferred embodiment of the present invention comprises the compounds of formula I wherein $R^1$, $R^2$, $R^3$ and $R^4$ which may be the same or different are each hydrogen, (lower)alkyl, (lower)alkenyl, (lower)alkoxy, hydroxy, carboxy, (lower)alkylthio, halogen, $CF_3$, amino, (lower)alkylamino, di(lower)alkylamino, phenyl or benzyl.

A more preferred embodiment of the present invention comprises the compounds of the formula

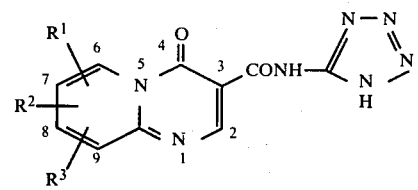

wherein $R^1$, $R^2$ and $R^3$ which may be the same or different are each hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O—(lower)alkenyl, —O—$(CH_2)_m$CH$(CH_2)_n$ in which m is 0 or an integer from 1 to 6 and n is an integer from 2 to 7, —OCH$_2$(CH$_2$)$_x$O(CH$_2$)$_y$CH$_3$ in which x and y are each independently 0 or an integer from 1 to 6, $CF_3$, hydroxy, hydroxymethyl, (lower)alkylthio, amino, nitro, $-N(CH_2)_r$ in which r is 4 or 5,

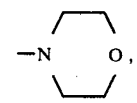

(lower)alkylamino, di(lower)alkylamino, carboxyl, -CO$_2$-(lower)alkyl, phenyl, phenyl substituted by one or two (lower)alkyl, (lower)alkoxy or halogen radicals, benzyl, (lower)alkylsulfinyl, $R^c$—CO— in which $R^c$ is (lower)alkyl, $R^c$—COO— in which $R^c$ is (lower)alkyl, —O(CH$_2$)$_k$OH in which k is an integer from 2 to 6,

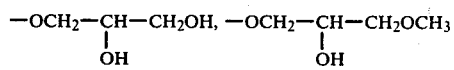

or —OCH$_2$C$_6$H$_5$, or wherein any two of $R^1$, $R^2$ and $R^3$ at positions 7 and 8 or 8 and 9 of the pyrido[1,2-a]pyrimidine ring system when taken together represent methylenedioxy or $(CH_2)_n$ in which n is 3, 4 or 5, and the pharmaceutically acceptable salts thereof, with the provisos that (1) no more than two of $R^1$, $R^2$ and $R^3$ are bulky (i.e. tertiary alkyl or tertiary alkoxy) groups, and when two of said $R^1$, $R^2$ and $R^3$ are bulky groups, they are located on non-adjacent positions; and (2) no more than two of $R^1$, $R^2$ and $R^3$ may be nitro or trifluoromethyl groups. Within this group of compounds, a preferred subgroup comprises those compounds where $R^1$, $R^2$ and $R^3$ are each independently hydrogen, (lower)alkyl, (lower)alkenyl, (lower)alkoxy, hydroxy, carboxy, (lower)alkylthio, halogen, $CF_3$, amino, (lower)alkylamino, di(lower)alkylamino, phenyl or benzyl. The $R^1$, $R^2$ and $R^3$ substituents of compound I' may be located at any of positions 6, 7, 8 or 9 of the pyrido[1,2-a]pyrimidine ring system as numbered above.

Another more preferred embodiment of the present invention comprises the compounds of the formula

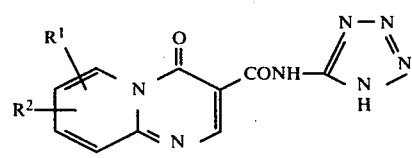

wherein $R^1$ and $R^2$ which may be the same or different are each hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O—(lower)alkenyl, —O—$(CH_2)_m CH[(CH_2)_n$ in which m is 0 or an integer from 1 to 6 and n is an integer from 2 to 7, —$OCH_2(CH_2)_x O(CH_2)_y CH_3$ in which x and y are each independently 0 or an integer from 1 to 6, $CF_3$, hydroxy, hydroxymethyl, (lower)alkylthio, amino, nitro, —$N[(CH_2)_r$ in which r is 4 or 5,

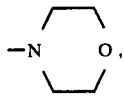

(lower)alkylamino, di(lower)alkylamino, carboxyl, —$CO_2$—(lower)alkyl, phenyl, phenyl substituted by one or two (lower)alkyl, (lower)alkoxy or halogen radicals, benzyl, (lower)alkylsulfinyl, $R^c$—CO— in which $R^c$ is (lower)alkyl, $R^c$—COO— in which $R^c$ is (lower)alkyl, —$O(CH_2)_k OH$ in which k is an integer from 2 to 6, —OCH$_2$—CH—CH$_2$OH, —OCH$_2$—CH—CH$_2$OCH$_3$
　　　　｜　　　　　　　　　　｜
　　　　OH　　　　　　　　　　OH or —$OCH_2C_6H_5$, or $R^1$ and $R^2$ when taken together at positions 7 and 8 or 8 and 9 of the pyrido[1,2-a]pyrimidine ring system are methylenedioxy or $(CH_2)_n$ in which n is 3, 4 or 5 and the pharmaceutically acceptable salts thereof, with the proviso that when $R^1$ and $R^2$ are both bulky (i.e. tertiary alkyl or tertiary alkoxy) groups, they are located on nonadjacent positions. Within this group of compounds, a preferred subgroup comprises those compounds wherein $R^1$ and $R^2$ are each independently hydrogen, (lower)alkyl, (lower)alkenyl, (lower)alkoxy, hydroxy, carboxy, (lower)alkylthio, halogen, $CF_3$, amino, (lower)alkylamino, di(lower)alkylamino, phenyl or benzyl. The $R^1$ and $R^2$ substituents of compound I″ may be located at any of positions 6, 7, 8 or 9 of the pyrido[1,2-a]pyrimidine ring system.

Another more preferred embodiment of the present invention comprises the compounds of the formula

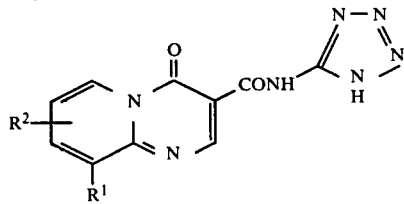

wherein $R^1$ and $R^2$ which may be the same or different are each hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, -O-(lower)alkenyl, —O—$(CH_2)_m CH[(CH_2)_n$ in which m is 0 or an integer from 1 to 6 and n is an integer from 2 to 7, —$OCH_2(CH_2)_x O(CH_2)_y CH_3$ in which x and y are each independently 0 or an integer from 1 to 6, $CF_3$, hydroxy, hydroxymethyl, (lower)alkylthio, amino, nitro, —$N[(CH_2)_r$ in which r is 4 or 5,

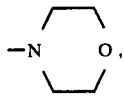

(lower)alkylamino, di(lower)alkylamino, carboxyl, —$CO_2$—(lower)alkyl, phenyl, phenyl substituted by one or two (lower)alkyl, (lower)alkoxy or halogen radicals, benzyl, (lower)alkylsulfinyl, $R^c$—CO— in which $R^c$ is (lower)alkyl, $R^c$—COO— in which $R^c$ is (lower)alkyl, —$O(CH_2)_k OH$ in which k is an integer from 2 to 6, —OCH$_2$—CH—CH$_2$OH, —OCH$_2$—CH—CH$_2$OCH$_3$
　　　　｜　　　　　　　　　　｜
　　　　OH　　　　　　　　　　OH or —$OCH_2C_6H_5$, or $R^1$ and $R^2$ when taken together at positions 8 and 9 of the pyrido[1,2-a]pyrimidine ring system are methylenedioxy or $(CH_2)_n$ in which n is 3, 4 or 5, and the pharmaceutically acceptable salts thereof, with the proviso that when both $R^1$ and $R^2$ are bulky (i.e. tertiary alkyl or tertiary alkoxy) groups, they are located on non-adjacent positions. Within this group of compounds, a preferred subgroup comprises those compounds wherein $R^1$ and $R^2$ are each independently hydrogen, (lower)alkyl, (lower)alkenyl, (lower)alkoxy, hydroxy, carboxy, (lower)alkylthio, halogen, $CF_3$, amino, (lower)alkylamino, di(lower)alkylamino, phenyl or benzyl. The $R^2$ substituent of compound I‴ may be located at any of positions 6, 7 or 8 of the pyrido[1,2-a]pyrimidine ring system.

Another more preferred embodiment of the present invention comprises the compounds of the formula

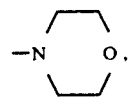

wherein $R^1$ and $R^2$ which may be the same or different are each hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O—(lower)alkenyl, —O—$(CH_2)_m CH[(CH_2)_n$ in which m is 0 or an integer from 1 to 6 and n is an integer from 2 to 7, —$OCH_2(CH_2)_x O(CH_2)_y CH_3$ in which x and y are each independently 0 or an integer from 1 to 6, $CF_3$, hydroxy, hydroxymethyl, (lower)alkylthio, amino, nitro, —$N[(CH_2)_r$ in which r is 4 or 5,

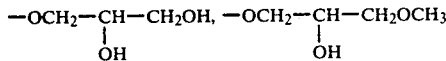

(lower)alkylamino, di(lower)alkylamino, carboxyl, —$CO_2$—(lower)alkyl, phenyl, phenyl substituted by one or two (lower)alkyl, (lower)alkoxy or halogen radicals, benzyl, (lower)alkylsulfinyl, $R^c$—CO— in which $R^c$ is (lower)alkyl, $R^c$—COO— in which $R^c$ is (lower)alkyl, —O(CH$_2$)$_k$OH in which k is an integer from 2 to 6,

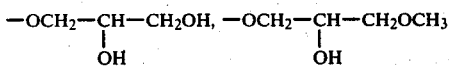

or —OCH$_2$C$_6$H$_5$, and the pharmaceutically acceptable salts thereof. Within this group of compounds, a preferred subgroup comprises those compounds wherein R$^1$ and R$^2$ are each independently hydrogen, (lower)alkyl, (lower)alkenyl, (lower)alkoxy, hydroxy, carboxy, (lower)alkylthio, halogen, CF$_3$, amino, (lower)alkylamino, di(lower)alkylamino, phenyl or benzyl.

Another more preferred embodiment of the present invention comprises the compounds of the formula

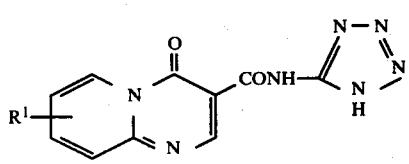

wherein R$^1$ is hydrogen, halogen, (lower)alkyl, cyclo(lower)alkyl, cyclo(lower)alkyl(lower)alkyl, (lower)alkenyl, (lower)alkynyl, (lower)alkoxy, (lower)alkoxy(lower)alkyl, —O—(lower)alkenyl, —O—(CH$_2$)$_m$CH(CH$_2$)$_n$ in which m is 0 or an integer from 1 to 6 and n is an integer from 2 to 7, —OCH$_2$(CH$_2$)$_x$O(CH$_2$)$_y$CH$_3$ in which x and y are each independently 0 or an integer from 1 to 6, CF$_3$, hydroxy, hydroxymethyl, (lower)alkylthio, amino, nitro, —N(CH$_2$)$_r$ in which r is 4 or 5,

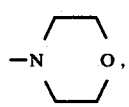

(lower)alkylamino, di(lower)alkylamino, carboxyl, —CO$_2$—(lower)alkyl, phenyl, phenyl substituted by one or two (lower)alkyl, (lower)alkoxy or halogen radicals, benzyl, (lower)alkylsulfinyl, R$^c$—CO— in which R$^c$ is (lower)alkyl, R$^c$—COO— in which R$^c$ is (lower)alkyl, —O(CH$_2$)$_k$OHin which k is an integer from 2 to 6,

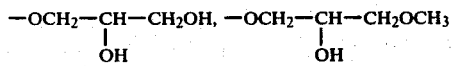

or —OCH$_2$C$_6$H$_5$, and the pharmaceutically acceptable salts thereof. Within this group of compounds, a preferred subgroup comprises the compounds wherein R$^1$ represents hydrogen, (lower)alkyl, (lower)alkenyl, (lower)alkoxy, hydroxy, carboxy, (lower)alkylthio, halogen, CF$_3$, amino, (lower)alkylamino, di(lower)alkylamino, phenyl or benzyl.

While the R$^1$ substituents in the compounds of formula I''''' may be located at any of positions 6, 7, 8 or 9 of the pyrido[1,2-a]pyrimidine ring system, the 7- and 9-substituted compounds are preferred. The most preferred monosubstituted compounds are those having the substituent at the 9-position.

The term "pharmaceutically acceptable salt" as used herein is intended to include non-toxic cationic salts such as the alkali metal salts, e.g., sodium and potassium, alkaline earth metal salts such as calcium, magnesium or barium, aluminum salts, ammonium salts, and salts with organic bases, e.g. amines such as triethylamine, n-propylamine, tri-n-butylamine, piperidine, ethanolamine, diethanolamine, triethanolamine, diethylaminoethylamine, ethylenediamine, N,N'-dibenzylethylenediamine, benzylamine, tris(hydroxymethyl)aminomethane, and pyrrolidine. Salt formation is accomplished by reacting the appropriate pyrido[1,2-a]pyrimidine-3-N-(1H-tetrazol-5-yl)carboxamide with a substantially equimolar amount of the appropriate base in an aqueous solution or in a suitable organic solvent such as methanol or ethanol. The salts are recovered by standard methods such as filtration if they are insoluble in the medium, or if they are soluble in the medium, by evaporation or by precipitation by addition of a non-solvent for the salt.

Those skilled in the art will appreciate that the compounds represented by formulae I-I''''' contain a tautomeric hydrogen atom and the compounds are thus capable of existing in both the 1H-tetrazol-5-yl form (see formula I$_a$ below) and the 2H-tetrazol-5-yl form (formula I$_b$ below).

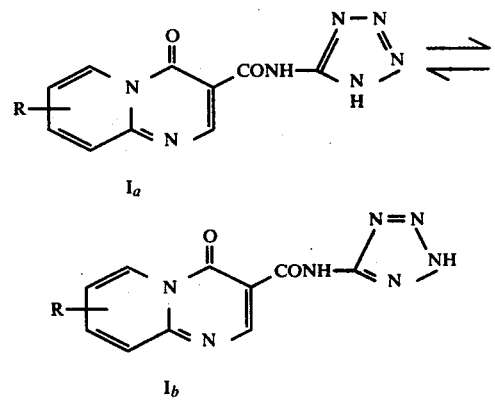

This invention embraces both forms, but for the sake of convenience, structure I$_a$ has been arbitrarily selected to represent the present compounds.

The compounds of formula I may be prepared by coupling of the appropriate 4-oxo-4H-pyrido[1,2-a]pyrimidine-3-carboxylic acid of the formula

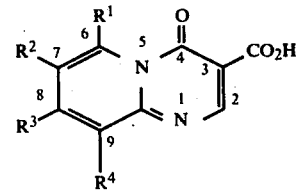

wherein R$^1$-R$^4$ are as defined above with 5-aminotetrazole of the formula

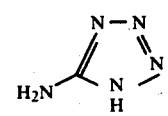

The coupling of the acid II with the aminotetrazole III may be accomplished with the aid of a variety of reagents commonly used, for example, in peptide synthesis. Examples of these reagents are described by Schröder and Lübke in "The Peptides", Vol. I, Academic Press, N.Y., 1965, pp. 77–128. The general principle of the synthesis is activation of the carboxyl group by either formation, for example, of the corresponding acid azide, acid halide (preferably the acid chloride), mixed anhydride (e.g. with carbonic acid monoesters), activated ester (e.g. p-nitrophenyl), or heterocyclic amide (e.g. imidazolide), or by treatment with a carbodiimide (e.g. N,N'-dicyclohexylcarbodiimide). Treatment of the activated carboxyl group with 5-aminotetrazole results in amide formation. The coupling reaction is carried out in a reaction-inert solvent system. The variety of coupling reagents which can be used allows a wide choice of solvents. Representative solvents are N,N-dimethylformamide, tetrahydrofuran, dioxane, methylene chloride, nitromethane, acetonitrile, dimethylsulfoxide, N,N-dimethylacetamide and hexamethylphosphoramide. Reaction times and temperatures are not critical. For good yields of products within a reasonable length of time, convenient temperatures are in the range of about 20°–100° C. for both steps, i.e. reaction of the acid with the coupling agent and reaction of the activated intermediate with the 5-aminotetrazole. The coupling reaction may be carried out either in stepwise fashion, i.e. by isolating the activated intermediate before addition of the 5-aminotetrazole, or by adding all reactants at once.

A preferred method of coupling utilizes N,N'-carbonyldiimidazole and is illustrated by the following scheme:

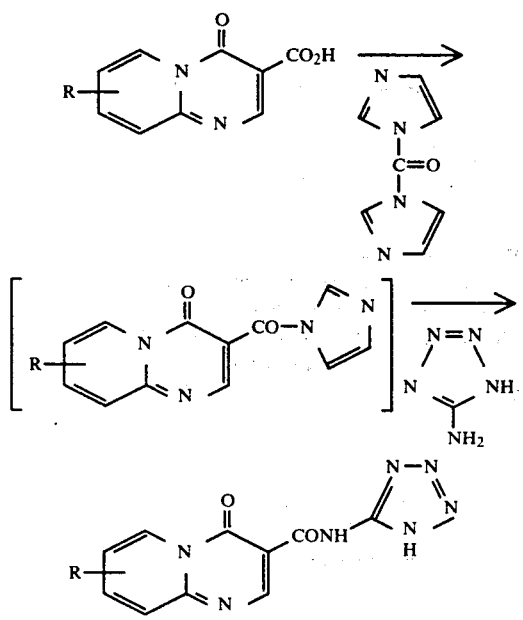

This reaction scheme may be carried out using the reaction-inert solvents mentioned above in both the imidazolide formation step and the step in which the imidazolide (either in situ or isolated) is reacted with the aminotetrazole. A preferred solvent is N,N-dimethylformamide. The reaction temperature is not critical, but a convenient temperature range for both steps has been found to be about 20°–100° C.

The 4-oxo-4H-pyrido[1,2-a]pyrimidine-3-carboxylic acids of formula II may be prepared by well-known methods. Typical general procedures are those described by Nishigaki et al., *J. Heterocycl. Chem.*, 8, 759 (1971); Okamoto et al., *Chem. Pharm. Bull.*, 22, 243(1974); Meszaros et al., U.S. Pat. No. 3,585,198; and R. Adams and I. J. Pachter, *J. Amer. Chem. Soc.*, 74, 5491 (1952). A preferred procedure, that of Nishigaki, is illustrated by the following reaction scheme:

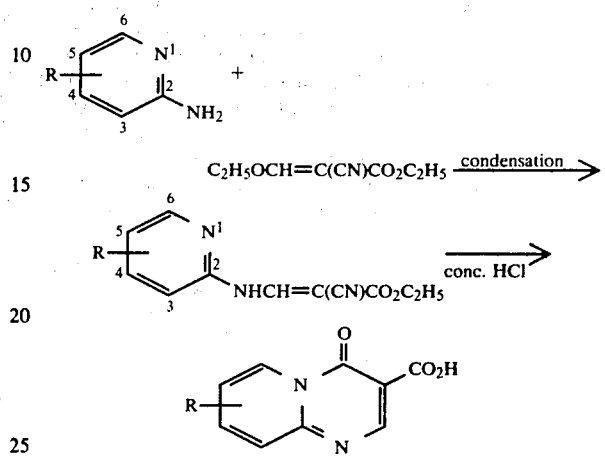

In this procedure the 2-aminopyridine compound is condensed with approximately an equimolar amount of ethyl ethoxymethylenecycanoacetate in the presence or absence of an inert organic solvent, e.g. an aromatic hydrocarbon such as toluene. The condensation is preferably carried out at elevated temperatures, e.g. 100° C. The acrylate intermediate is then refluxed with a concentrated hydrochloric acid solution to form the carboxylic acid starting material of formula II.

In using the above-described processes to prepare compounds of formula I in which $R^1$, $R^2$, $R^3$ or $R^4$ contain free hydroxy, amino or carboxyl groups, it is of course understood that such groups will be protected by suitable known protecting groups during the reaction steps beginning with the basic 2-aminopyridine starting materials through the formation of the final amides. The protecting group(s) may then be removed by methods known per se to give the desired products having the unprotected substituent groups. Amino-substituted compounds may be prepared from the corresponding nitro-substituted product by catalytic hydrogenation. In preparing compounds of formula I where $R^1$, $R^2$, $R^3$ or $R^4$ are (lower)alkylamino or di(lower)alkylamino, the corresponding amino-substituted compound may first be prepared and then alkylated. Alternatively, the dialkylaminosubstituted compounds can be prepared directly from the appropriate 2-aminopyridine starting material.

The 2-aminopyridine starting materials are known compounds or may be prepared by methods well-known in the art.

In another aspect, the present invention provides a method of inhibiting or preventing the symptoms of an allergic reaction such as bronchial asthma, allergic rhinitis, urticaria, allergic conjunctivitis, systemic anaphylaxis, atopic dermatitis and food allergy in a mammal susceptible to such a reaction which comprises administering to said mammal a prophylactically effective dose of a compound of formula I or a pharmaceutically acceptable salt thereof.

The compounds of the present invention may be administered either as individual therapeutic agents or as mixtures with other therapeutic agents. They may be administered alone but are generally administered in the form of pharmaceutical compositions, i.e. mixtures of the active agents with suitable pharmaceutical carriers or diluents. Examples of such compositions include tablets, lozenges, capsules, powders, aerosol sprays, aqueous or oily suspensions, syrups, elixers and aqueous solutions. The compounds are preferably administered orally, but may also be administered by inhalation, injection, instillation or by implantation for controlled drug release from a solid carrier reservoir.

The nature of the pharmaceutical composition and the pharmaceutical carrier or diluent will, of course, depend on the desired route of administration. For example, oral compositions may be in the form of tablets or capsules and may contain conventional excipients such as binding agents (e.g. syrup, acacia, gelatin, sorbitol, tragacanth or polyvinylpyrrolidone), fillers (e.g. lactose, sugar, maize-starch, calcium phosphate, sorbitol or glycine), lubricants (e.g. magnesium stearate, talc, polyethylene glycol, or silica) disintegrants (e.g. starch) or wetting agents (e.g. sodium lauryl sulfate). Oral liquid preparations may be in the form of aqueous or oily suspensions, solutions, emulsions, syrups, elixers, etc. or may be presented as a dry product for reconstitution with water or other suitable vehicle before use. Such liquid preparations may contain conventional additives such as suspending agents, flavoring agents, diluents or emulsifying agents. For parenteral administration, inhalation or instillation, solutions or suspensions of a compound of formula I with conventional pharmaceutical vehicles may be employed, e.g. as an aerosol spray for inhalation, as an aqueous solution for intravenous injection or instillation, or as an oily suspension for intramuscular injection. The compounds may also be administered by means of inhalers or other devices which permit the active compounds in the form of dry powders to come into direct contact with the lungs.

The compounds of the present invention or pharmaceutical compositions thereof may be administered to human allergic patients in single oral doses of approximately 0.5–500 mg. of active ingredient and multiple oral doses totalling up to about 1000 mg./day of active ingredient. When administered by inhalation or instillation, lower doses are generally given, i.e. on the order of about 0.1 of the normal oral dosage for the particular compound in question. These values are illustrative only, however, and the physician of course will ultimately determine the dosage most suitable for a particular patient on the basis of factors such as age, weight, severity of the symptoms and the particular agent to be administered.

The in vivo animal model studies descibed below indicate that the compounds of formula I are highly potent antiallergy agents.

BIOLOGICAL ACTIVITY DATA

The reagin-mediated rat Passive Cutaneous Anaphylaxis (PCA) screening test used to evaluate the present compounds is generally regarded as one of the best animal models for use in predicting the antiallergy activity of test compounds in man. This screen provides a measure of the effectiveness of test compounds in either inhibiting the release or antagonizing the action of mediators arising from the interaction of reaginic antibodies with specific antigen, mediators which are causative factors in allergic disorders. The details of the test are fully described in U.S. Pat. No. 4,031,093.

The test compounds were solubilized in aqueous sodium bicarbonate and administered intravenously (i.v.) or per os (p.o.) either one or ten minutes, respectively, prior to antigen challenge. Disodium cromoglycate (DSCG), solubilized in saline, was administered i.v. at the time of challenge and p.o 30 minutes prior to challenge. Test results for some representative compounds of the present invention are given in the table below in terms of the $ID_{50}$ value, i.e. the dose of compound that inhibits 50% of the response.

Table 1

Rat PCA Screening Data for 4-Oxo-4H-pyrido[1,2-a]pyrimidine-3-N-(1H-tetrazol-5-yl)carboxamides Compound

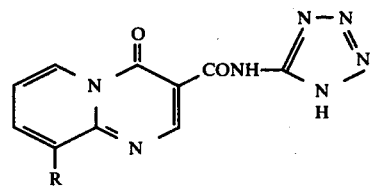

| Example No. | R | $ID_{50}$ in mg./kg. i.v. | p.o. |
|---|---|---|---|
| 1 | H |  | 0.2 |
| 2 | CH$_3$ | 0.04 | 0.1 |
| 3 | C$_2$H$_5$ |  | 0.1 |
| DSCG |  | 0.6 | >>30 |

The following examples are provided solely for the purpose of illustrating preparation of the starting materials and compounds of the present invention and are not to be construed as limitations of the invention. All temperatures referred to below are in degrees Celsius. "Skellysolve B" is a petroleum ether fraction of b.p. 60°–68° C. consisting essentially of n-hexane (trade name of Skelly Oil Co.).

PREPARATION OF STARTING MATERIALS

Preparation 1: 2-Amino-5-ethylpyridine a. Benzyl (5-Ethyl-2-pyridyl)carbamate

Diphenylphosphoryl azide (4.04 g., 14.7 mmoles) was added to a solution of 5-ethylpyridine-2-carboxylic acid (2.22 g., 14.7 mmoles), triethylamine (1.485 g., 14.7 mmoles), and benzyl alcohol (1.75 g., 16.17 mmoles) in 1,4-dioxane (23.5 ml.), and the mixture heated under reflux for one hour. The 1,4-dioxane was removed under reduced pressure. A solution of the residue in toluene was washed successively with water, aqueous sodium bicarbonate, and brine, and was then dried over sodium sulfate. The toluene was removed and the residue recrystallized from 2-propanol to give benzyl (5-ethyl-2-pyridyl)carbamate (1.9 g., 50.5%), m.p. 125°–127°. An analytical sample had m.p. 127°–130°.

Anal. Calcd for $C_{15}H_{16}N_2O_2$: C, 70.29; H, 6.29; N, 10.93. Found: C, 70.01; H, 6.32; N, 10.72.

b. 2-Amino-5-ethylpyridine

A suspension of benzyl (5-ethyl-2-pyridyl)carbamate (1.9 g., 7.43 mmoles) and 10% palladium-on-carbon (0.4 g.) in ethanol (100 ml.) was shaken with hydrogen at a pressure of 3.5 kg./cm$^2$ for 2 hours. The catalyst was removed by filtration and the filtrate concentrated to yield 2-amino-5-ethylpyridine (0.9 g., 99.4%) as a colorless oil.

Preparation 2: 2-Amino-5-n-butylpyridine a. Benzyl (5-n-Butyl-2-pyridyl)carbamate Diphenylphosphoryl azide (1.5 g., 5.58 mmoles) was added to a solution of 5-n-butylpyridine-2-carboxylic acid (1.0 g., 5.58 mmoles), triethylamine (0.565 g., 5.58 mmoles), and benzyl alcohol (0.663 g., 6.12 mmoles) in 1,4-dioxane (9.0 ml.) at 25°. The stirred solution was heated until an exothermic reaction began. When the exothermic reaction had subsided, the solution was heated under reflux for 1.5 hours. The reaction mixture was concentrated and the residue dissolved in toluene. This solution was washed successively with water, 10% aqueous sodium bicarbonate, and brine, and then dried over sodium sulfate. The solution was concentrated and the residue recrystallized from 2-propanol to give the title compound (0.91 g., 57%), m.p. 142°–143°.

Anal. Calcd for $C_{17}H_{20}N_2O_2$: C, 71.80; H, 7.09; N, 9.85. Found: C, 71.72; H, 6.85; N, 9.87.

b. 2-Amino-5-n-butylpyridine

A mixture of benzyl (5-n-butyl-2-pyridyl)carbamate (6.5 g. 22.86 mmoles) and 10% palladium on carbon (2.7 g.) in ethanol (400 ml.) was shaken at room temperature for 2 hours in an atmosphere of hydrogen at an initial pressure of 3.52 kg./cm.$^2$ The mixture was filtered and the filtrate reduced to dryness to leave 2-amino-5-n-butylpyridine (3.42 g., 99.7%), m.p. 30°–33° (lit. m.p. 35°–36° in *Helv. Chim. Acta,* 39, 505 (1956).

Preparation 3: 2-Amino-5-phenylpyridine

A solution of 2-chloro-5-phenylpyridine (4.0 g., 0.021 mole) in dry diethyl ether (160 ml.) was added dropwise to a solution of sodium (3.39 g., 0.15 g-atom) in liquid ammonia (160 ml.) containing ferrous nitrate hexahydrate (0.095 g.). The resulting suspension was allowed to reflux for 4 hours. Ammonium chloride was added and the ammonia allowed to evaporate. The residue was treated with 5% aqueous sodium hydroxide (5 ml.). The mixture was filtered. The aqueous layer was extracted with ether (2×100 ml.). The combined ethereal layers were washed with brine and dried over sodium sulfate. The solution was concentrated and the residue recrystallized from methylcyclohexane. The product was triturated with chloroform (100 ml.). The mixture was filtered and the filtrate evaporated to give 2-amino-5-phenylpyridine (1.3 g., 36%), m.p. 133°–135° (lit. m.p. 133° in *Chem. Ber.,* 91, 247 (1958).

Preparation 4: 2-Amino-3,5-dimethylpyridine

Ferrous nitrate hexahydrate (60 mg.) followed by sodium (4.5 g., 0.196 g-atom) were added to liquid ammonia. To this mixture was added a solution of 3,5-dimethylpyridine (10.0 g., 0.093 mole) in N,N-dimethylaniline (21 ml.) over a period of 5 minutes. The ammonia was allowed to evaporate and the residue heated under nitrogen by means of an oil bath maintained at 180° for 18 hours. The cooled residue was treated with ice (50 g.) followed by 2 N sodium hydroxide (50 ml.). The mixture was triturated for 2 hours and then filtered. The collected solid was washed with boiling toluene (2×100 ml.). The toluene layer was separated from the combined filtrate and washings, concentrated to about 50 ml. and extracted with 5% aqueous acetic acid (5×20 ml.). The combined extracts were filtered and reduced to dryness. The residue was recrystallized from methylcyclohexane to give 2-amino-3,5-dimethylpyridine acetate (4.9 g., 29%), m.p. 85°–95°.

The acetate (2.5 g., 1.37 mmoles) was briefly suspended in 1 N sodium hydroxide (50 ml.). The mixture was extracted with methylene chloride. The extract was washed with water, dried, and concentrated to give 2-amino-3,5-dimethylpyridine as an oil.

Preparation 5: Ethyl 2-Cyano-3-(3-ethyl-2-pyridylamino)acrylate

A solution of 2-amino-3-ethylpyridine (13.0 g., 0.1063 mole) and ethyl ethoxymethylenecyanoacetate (18.0 g., 0.1063 mole) in toluene (50 ml.) was heated on a steam bath for 20 minutes. The solution was cooled and the resulting mixture diluted with Skellysolve B. The title compound (19.0 g.), m.p. 122°–125° C., was collected by filtration. From the mother liquors, after recrystallization from cyclohexane, was obtained a further crop (7.0 g.) of product, m.p. 122°–125° C. Total yield of title compound, 26.0 g. (99.6%). The material from cyclohexane was recrystallized twice from methanol to give analytical material, m.p. 123°–125° C.

Anal. Calcd for $C_{13}H_{15}N_3O_2$: C, 63.66; H, 6.16; N, 17.13. Found: C, 63.49; H, 6.18; N, 17.13.

Preparation 6: Ethyl 2-Cyano-3-(5-methyl-2-pyridylamino)acrylate

A mixture of 2-amino-5-methylpyridine (5.0 g., 46.2 mmoles) and ethyl ethoxymethylenecyanoacetate (7.82 g., 46.2 mmoles) was heated by means of an oil bath maintained at 100° for 15 minutes. The mixture was cooled and the resultant solid recrystallized from acetonitrile to give the title compound (5.4 g., 50.5%), m.p. 170°–171.5°.

Anal. Calcd. for $C_{12}H_{13}N_3O_2$: C, 62.32; H, 5.67; N, 18.17. Found: C, 62.44; H, 5.74; N, 18.05.

Preparation 7: Ethyl 2-Cyano-3-(5-ethyl-2-pyridylamino)acrylate

The title compound (m.p. 155°–156°, 25.4% yield) was prepared from 2-amino-5-ethylpyridine and ethyl ethoxymethylenecyanoacetate in a manner similar to that described for the preparation of ethyl 2-cyano-3-(5-methyl-2-pyridylamino)acrylate in Preparation 6.

Anal. Calcd. for $C_{13}H_{15}N_3O_2$: C, 63.66; H, 6.16; N, 17.13. Found: C, 63.54; H, 6.09; N, 17.02.

Preparation 8: Ethyl 2-Cyano-3-(5-n-butyl-2-pyridylamino)acrylate

A solution of 2-amino-5-n-butylpyridine (3.72 g., 23.43 mmoles) and ethyl ethoxymethylenecyanoacetate (3.96 g., 23.43 mmoles) in toluene was heated for 10 minutes by means of an oil bath maintained at 100°. The solution was cooled and treated with Skellysolve B (200 ml.). The mixture was triturated for 18 hours at room temperature and then filtered. The collected title compound (4.3 g., 67.2%) had m.p. 69°–73°.

Preparation 9: Ethyl 2-Cyano-3-(5-phenyl-2-pyridylamino)acrylate

A mixture of 2-amino-5-phenylpyridine (1.19 g., 6.99 mmoles) and ethyl ethoxymethylenecyanoacetate (1.18 g., 6.99 mmoles) was fused at an oil bath temperature of 100° for 15 minutes. The product was recrystallized from toluene to give the title compound (1.3 g.), m.p. 126°–134°. An additional crop of product (0.3 g.), m.p. 119°–126° was obtained from the mother liquors. Total yield of product, 1.6 g. (78%).

Preparation 10: Ethyl 2-Cyano-3-(3-methyl-2-pyridylamino)acrylate

A solution of 2-amino-3-methylpyridine (5.0 g., 0.0462 mole) and ethyl ethoxymethylenecyanoacetate (7.82 g., 0.0462 mole) in toluene (4 ml.) was heated for 15 minutes by means of an oil bath maintained at 100°. The solution was cooled and the title compound (9.1 g., 85%) collected by filtration. The product, m.p. 139°–143°, was recrystallized from 2-propanol to give an analytical sample, m.p. 144°–146°.

Anal. Calcd for $C_{12}H_{13}N_3O_2$: C, 62.32; H, 5.67; N, 18.17. Found: C, 61.87; H, 5.63; N, 18.42.

Preparation 11: Ethyl 2-Cyano-3-(3,5-dimethyl-2-pyridylamino)acrylate

The title compound (79% yield), m.p. 156°–159° from methylcyclohexane, was prepared in a manner similar to that described for the preparation of ethyl 2-cyano-3-(3-methyl-2-pyridylamino)acrylate in Preparation 10.

Anal. Calcd for $C_{13}H_{15}N_3O_2$: C, 63.66; H, 6.16; N, 17.13. Found: C, 63.94; H, 6.24; N, 16.78.

Preparation 12: 9-Ethyl-4-oxo-4H-pyrido]1,2-a]pyrimidine-3-carboxylic Acid

A mixture of ethyl 2-cyano-3-(3-ethyl-2-pyridylamino)acrylate (4.0 g., 16.3 mmoles) and concentrated hydrochloric acid (20 ml.) was heated under reflux for 40 minutes. The solution was reduced to dryness under vacuum and the residue dried over phosphorous pentoxide. The residue was triturated with acetonitrile. The mixture was filtered and the collected solid recrystallized from water to give the title compound (1.37 g., 38.6%), m.p. 157°–159° C.

Anal. Calcd for $C_{11}H_{10}N_2O_3$: C, 60.54; H, 4.62; N, 12.84. Found: C, 60.69; H, 4.64; N, 12.74.

Following the general procedure of Preparation 12, the following 4-oxo-4H-pyrido[1,2-a]pyrimidine-3-carboxylic acids are prepared from the indicated acrylates:

| Acrylate | Acid Product |
| --- | --- |
| ethyl 2-cyano-3-(5-methyl-2-pyridylamino)acrylate | 7-methyl-4-oxo-4H-pyrido[1,2-a]pyrimidine-3-carboxylic acid |
| ethyl 2-cyano-3-(5-ethyl-2-pyridylamino)acrylate | 7-ethyl-4-oxo-4H-pyrido[1,2-a]pyrimidine-3-carboxylic acid |
| ethyl 2-cyano-3-(5-n-butyl-2-pyridylamino)acrylate | 7-n-butyl-4-oxo-4H-pyrido[1,2-a]pyrimidine-3-carboxylic acid |
| ethyl 2-cyano-3-(5-phenyl-2-pyridylamino)acrylate | 7-phenyl-4-oxo-4H-pyrido[1,2-a]pyrimidine-3-carboxylic acid |
| ethyl 2-cyano-3-(3,5-dimethyl-2-pyridylamino)acrylate | 7,9-dimethyl-4-oxo-4H-pyrido-[1,2-a]pyrimidine-3-carboxylic acid |
| ethyl 2-cyano-3-(4-methyl-2-pyridylamino)acrylate | 8-methyl-4-oxo-4H-pyrido[1,2-a]pyrimidine-3-carboxylic acid |

EXAMPLE 1

4-Oxo-4H-pyrido[1,2-a]pyrimidine-3-N-(1H-tetrazol-5-yl)carboxamide ($R^1$-$R^4$=H)

A mixture of 4-oxo-4H-pyrido[1,2-a]pyrimidine-3-carboxylic acid[1] (2.0 g., 10.5 mmoles) and N,N'-carbonyldiimidazole (1.87 g., 11.5 mmoles) in N,N-dimethylformamide (90 ml.) was heated on a steam bath for 15 minutes and then allowed to stand at room temperature for 45 minutes. 5-Aminotetrazole (0.98 g., 11.5 mmoles) was added and the mixture heated on a steam bath for 40 minutes. The cooled mixture was filtered and the collected solid recrystallized from N,N-dimethylformamide to give the title compound (1.29 g., 47.5%), m.p. 336°–337° C. (decomp.).

[1]Nishigaki et al., *J. Heterocycl. Chem.*, 8, 759 (1971).

Anal. Calcd for $C_{10}H_7N_7O_2$: C, 46.70; H, 2.74; N, 38.20. Found: C, 46.74; H, 2.76; N, 37.82.

EXAMPLE 2

9-Methyl-4-oxo-4H-pyrido[1,2-a]pyrimidine-3-N-(1H-tetrazol-5-yl)carboxamide ($R^1$-$R^3$=H, $R^4$=$CH_3$)

In a manner similar to that described in Example 1, the title compound was prepared from 9-methyl-4-oxo-4H-pyrido[1,2-a]pyrimidine-3-carboxylic acid[2] in 78% yield. Recrystallization from N,N-dimethylformamide gave product with m.p. 319°–320° C. (decomp.)

[2]Okamoto et al., *Chem. Pharm. Bull.*, 22, 243 (1974).

Anal. Calcd for $C_{11}H_9N_7O_2$: C, 48.71; H, 3.34; N, 36.15. Found: C, 48.45; H, 3.19; N, 36.39.

EXAMPLE 3

9-Ethyl-4-oxo-4H-pyrido[1,2-a]pyrimidine-3-N-(1H-tetrazol-5-yl)carboxamide ($R^1$-$R^3$=H, $R^4$=$C_2H_5$)

In a manner similar to that described in Example 1, the title compound was prepared from 9-ethyl-4-oxo-4H-pyrido[1,2-a]pyrimidine-3-carboxylic acid in 59% yield. Recrystallization from N,N-dimethylformamide gave product with m.p. 292°–293° C. (decomp.).

Anal. Calcd for $C_{12}H_{11}N_7O_2$: C, 50.52; H, 3.89; N, 34.37. Found: C, 50.51; H, 3.90; N, 34.14.

EXAMPLE 4

7-Methyl-4-oxo-4H-pyrido[1,2-a]pyrimidine-3-N-(1H-tetrazol-5-yl)carboxamide ($R^1$, $R^3$, $R^4$=H; $R^2$=$CH_3$)

Following the general procedure of Example 1, the title product is prepared from 7-methyl-4-oxo-4H-pyrido-[1,2-a]pyrimidine-3-carboxylic acid.

EXAMPLE 5

7-Ethyl-4-oxo-4H-pyrido[1,2-a]pyrimidine-3-N-(1H-tetrazol-5-yl)carboxamide ($R^1$, $R^3$, $R^4$=H; $R^2$=$C_2H_5$)

Following the general procedure of Example 1, the title product is prepared from 7-ethyl-4-oxo-4H-pyrido-[1,2-a]pyrimidine-3-carboxylic acid.

EXAMPLE 6

7-n-Butyl-4-pyrido[1,2-a]pyrimidine-3-N-(1H-tetrazol-5-yl)carboxamide ($R^1$, $R^3$, $R^4$=H; $R^2$=n-butyl)

Following the general procedure of Example 1, the title product is prepared from 7-n-butyl-4-oxo-4H-pyrido-[1,2-a]pyrimidine-3-carboxylic acid.

EXAMPLE 7

7-Phenyl-4-oxo-4H-pyrido[1,2-a]pyrimidine-3-N-(1H-tetrazol-5-yl)carboxamide ($R^1$, $R^3$, $R^4$=H; $R^2$=$C_6H_5$ Following the general procedure of Example 1, the title product is prepared from 7-phenyl-4-oxo-4H-pyrido[1,2-a]pyrimidine-3-carboxylic acid.

EXAMPLE 8

7,9-Dimethyl-4-oxo-4H-pyrido[1,2-a]pyrimidine-3-N-(1H-tetrazol-5-yl)carboxamide ($R^1$, $R^3$=H; $R^2$, $R^4$=$CH_3$)

Following the general procedure of Example 1, the title product is prepared from 7,9-dimethyl-4-oxo-4H-pyrido[1,2-a]pyrimidine-3-carboxylic acid.

EXAMPLE 9

8-Methyl-4-oxo-4H-pyrido[1,2-a]pyrimidine-3-N-(1H-tetrazol-5-yl)carboxamide ($R^3=CH_3$; $R^1$, $R^2$, $R^4=H$)

Following the general procedure of Example 1, the title product is prepared from 8-methyl-4-oxo-4H-pyrido[1,2-a]pyrimidine-3-carboxylic acid.

EXAMPLE 10

Following the general procedures of Examples 1–9, the following compounds may be prepared by use of the appropriate 2-aminopyridine starting material.

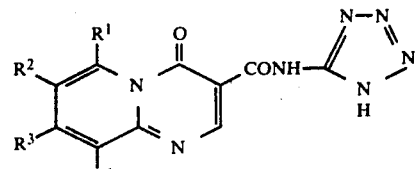

| $R^1$ | $R^2$ | $R^3$ | $R^4$ |
|---|---|---|---|
| H | Cl | H | H |
| CH$_3$ | H | H | H |
| H | CO$_2$H | H | H |
| H | NO$_2$ | H | H |
| H | $^a$NH$_2$ | H | H |
| H | H | H | CH$_3$O |
| H | H | H | CH$_3$OCH$_2$CH$_2$ |
| H | H | H | Cl |
| H | H | H | (CH$_3$)$_2$CH |
| H | C$_2$H$_5$ | H | C$_2$H$_5$ |
| H | NO$_2$ | H | CH$_3$ |
| H | H | H | $^b$OH |
| H | H | H | HOCH$_2$ |
| H | H | CH$_3$ | CH$_3$ |
| H | Cl | H | Cl |
| H | H | H | C$_6$H$_5$ |
| H | H | H | C$_6$H$_5$CH$_2$ |
| H | H | H | p-chlorophenyl |
| H | H | H | o-methylphenyl |
| H | H | H | o-ethylphenyl |
| H | H | H | m-methoxyphenyl |
| H | H | H | p-ethoxyphenyl |
| H | H | H | o-bromophenyl |
| H | H | H | 3-chloro-4-methylphenyl |
| H | H | H | 3,4-dimethoxyphenyl |
| H | C$_6$H$_5$CH$_2$ | H | H |
| H | p-chlorophenyl | H | H |
| CH$_3$O | H | H | H |
| H | Br | H | H |
| H | Br | H | Br |
| C$_2$H$_5$O | H | H | H |
| H | H | Cl | H |
| Br | H | H | H |
| CH$_3$ | H | CH$_3$ | H |
| H | $^b$OH | H | H |
| H | CH$_3$SO | H | H |
| H | H | H | NO$_2$ |
| H | n-C$_3$H$_7$ | H | H |
| H | CH$_2$=CHCH$_2$ | H | H |
| H | CH≡CCH$_2$ | H | H |
| H | (CH$_3$)$_2$CH | H | H |
| H | (CH$_3$)$_3$C | H | H |
| H | (CH$_3$)$_2$CHCH$_2$ | H | H |
| H | C$_2$H$_5$CH(CH$_3$) | H | H |
| H | H | H | n-C$_3$H$_7$ |
| H | H | H | n-C$_4$H$_9$ |
| H | H | H | (CH$_3$)$_2$CHCH$_2$ |
| H | H | H | C$_2$H$_5$CH(CH$_3$) |
| H | H | H | (CH$_3$)$_3$C |
| H | H | H | n-C$_5$H$_{11}$ |
| H | H | H | n-C$_6$H$_{13}$ |
| H | H | C$_2$H$_5$O | H |
| $^b$OH | H | CH$_3$ | Br |
| H | H | Cl | CH$_3$ |
| CH$_3$ | Cl | H | Cl |
| H | H | CH$_3$ | F |
| H | Cl | CH$_3$ | Cl |
| H | H | F | CH$_3$ |
| H | Br | C$_2$H$_5$ | Br |
| NO$_2$ | H | CH$_3$ | CH$_3$ |
| CH$_3$ | CH$_3$ | CH$_3$ | CH$_3$ |
| NO$_2$ | H | H | Br |
| CH$_3$ | H | CH$_3$ | Cl |
| NO$_2$ | H | Br | Br |
| CH$_3$ | Cl | CH$_3$ | H |
| CH$_3$ | Cl | CH$_3$ | Cl |
| H | H | H | C$_2$H$_5$O |
| H | H | H | n-C$_3$H$_7$O |
| H | H | H | (CH$_3$)$_2$CHO |
| H | H | H | n-C$_4$H$_9$O |
| H | H | H | (CH$_3$)$_3$CO |
| H | H | H | CH$_3$CH$_2$(CH$_3$)CHO |
| H | H | H | (CH$_3$)$_2$CHCH$_2$O |
| H | H | H | CH$_2$=CH—CH$_2$O |
| H | H | H | ▷—CH$_2$ |
| H | H | H | ▷—CH$_2$O |
| H | H | H | CO$_2$H |
| H | H | H | $^a$NH$_2$ |
| H | H | H | CH$_3$S |
| H | H | H | C$_2$H$_5$S |
| H | H | H | $^c$CH$_3$NH |
| H | H | H | $^c$C$_2$H$_5$NH |
| H | H | H | (CH$_3$)$_2$N |
| H | H | H | CF$_3$ |
| H | H | H | CH=CHCH$_2$ |
| H | H | H | CH$_2$=CH |
| H | H | H | CH≡C |
| H | H | H | CH≡CCH$_2$ |
| H | H | H | CH$_2$=CHO |
| H | H | H | ▷—O |
| H | H | H | CH$_3$OCH$_2$O |
| H | H | H | CH$_3$OCH$_2$CH$_2$O |
| H | H | H | —N⟨morpholino⟩O |
| H | H | H | —N⟨pyrrolidino⟩ |
| H | H | H | —N⟨piperidino⟩ |
| H | H | H | ⟨1,3-dioxolan-2-yl-CH₂⟩ |
| H | H | H | ⟨1,3-dioxolan-2-yl⟩ |

-continued

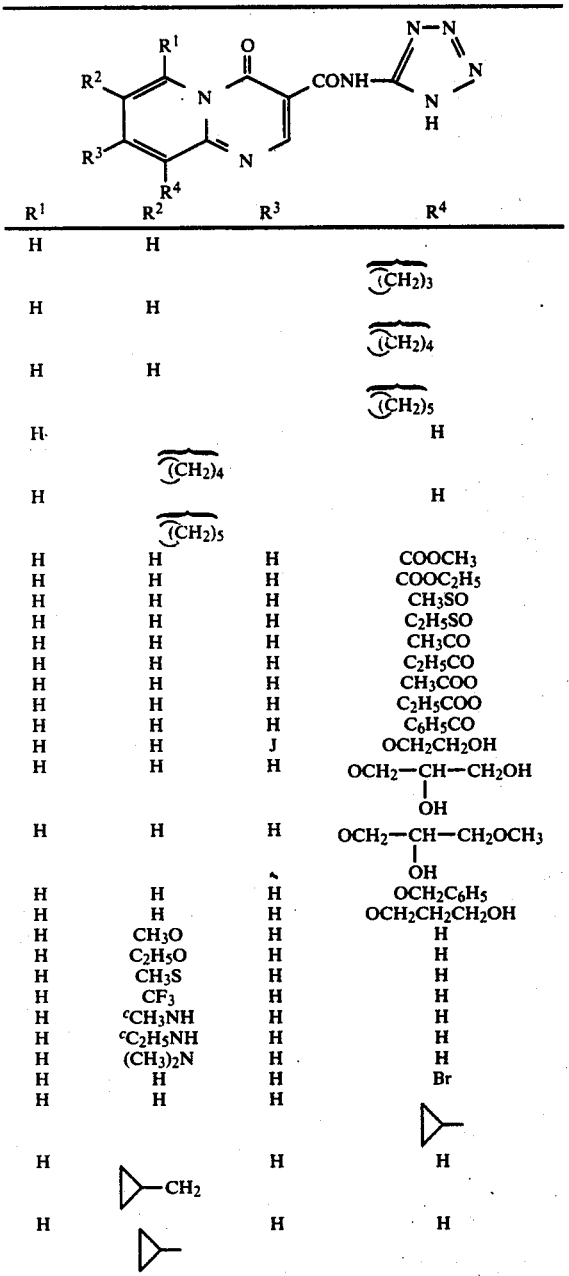

| R¹ | R² | R³ | R⁴ |
|---|---|---|---|
| H | H | \_(CH₂)₃\_ | |
| H | H | \_(CH₂)₄\_ | |
| H | H | \_(CH₂)₅\_ | |
| H | \_(CH₂)₄\_ | | H |
| H | \_(CH₂)₅\_ | | H |
| H | H | H | COOCH₃ |
| H | H | H | COOC₂H₅ |
| H | H | H | CH₃SO |
| H | H | H | C₂H₅SO |
| H | H | H | CH₃CO |
| H | H | H | C₂H₅CO |
| H | H | H | CH₃COO |
| H | H | H | C₂H₅COO |
| H | H | H | C₆H₅CO |
| H | H | J | OCH₂CH₂OH |
| H | H | H | OCH₂—CH—CH₂OH<br>\|<br>OH |
| H | H | H | OCH₂—CH—CH₂OCH₃<br>\|<br>OH |
| H | H | H | OCH₂C₆H₅ |
| H | H | H | OCH₂CH₂CH₂OH |
| H | CH₃O | H | H |
| H | C₂H₅O | H | H |
| H | CH₃S | H | H |
| H | CF₃ | H | H |
| H | ᶜCH₃NH | H | H |
| H | ᶜC₂H₅NH | H | H |
| H | (CH₃)₂N | H | H |
| H | H | H | Br |
| H | H | H | ▷— |
| H | ▷—CH₂ | H | H |
| H | ▷— | H | H |

ᵃprepared from corresponding nitro-substituted compound by catalytic reduction
ᵇprepared from corresponding protected-hydroxy compound (e.g. benzyloxy or methoxy) via removal of protecting group (e.g. hydrogenolysis for benzyloxy or treatment with a dealkylating agent (such as hydrobromic acid) for methoxy)
ᶜprepared by alkylation of corresponding amino-substituted compound

EXAMPLE 11

9-Methyl-4-oxo-4H-pyrido[1,2-a]pyrimidine-3-N-(1H-tetrazol-5-yl)carboxamide, Sodium Salt.

To a solution of 9-methyl-4-oxo-4H-pyrido[1,2-a]pyrimidine-3-N-(1H-tetrazol-5-yl)carboxamide in water is added about one molar equivalent of aqueous sodium hydroxide. The reaction mixture is filtered, and the title salt is obtained by lyophilization of the filtrate.

Replacement of the 9-methyl-4-oxo-4H-pyrido[1,2-a]pyrimidine-3-N-(1H-tetrazol-5-yl)carboxamide in the above procedure with an equimolar weight of the other 4-oxo-4H-pyrido[1,2-a]pyrimidine-3-N-(1H-tetrazol-5-yl)carboxamide compounds prepared in Examples 1 and 3–10 above gives the corresponding sodium salts for each of the indicated compounds.

Replacement of the sodium hydroxide in the above procedure with other bases, e.g. KOH, Ca(OH)₂, Mg(OH)₂ or NH₄OH gives the corresponding base addition salts.

Reaction of the 4-oxo-4H-pyrido[1,2-a]pyrimidine-3-N-(1H-tetrazol-5-yl)carboxamide compounds of Examples 1–10 with ethanolamine, ethylenediamine, diethanolamine, triethanolamine or tris(hydroxymethyl)aminomethane gives the corresponding amine salts for each of the indicated compounds.

I claim:

1. A compound of the formula

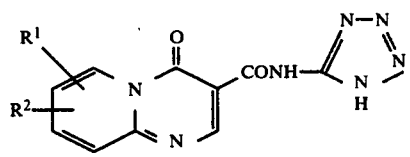

wherein $R^1$ and $R^2$ which may be the same or different are each hydrogen, halogen, (lower)alkyl, (lower)alkenyl, (lower)alkynyl, (lower)alkoxy, $CF_3$, hydroxy, (lower)alkylthio, amino, nitro, (lower)alkylamino, di(lower)alkylamino, carboxyl, phenyl, or (lower)alkylsulfinyl, or a pharmaceutically acceptable salt thereof, with the proviso that when $R^1$ and $R^2$ are tertiary alkyl or tertiary alkoxy groups, they are located on non-adjacent positions.

2. A compound of claim 1 wherein $R^1$ and $R^2$ are each independently hydrogen, (lower)alkyl, (lower)alkenyl, (lower)alkoxy, hydroxy, (lower)alkylthio, halogen, $CF_3$, or amino.

3. A compound of the formula

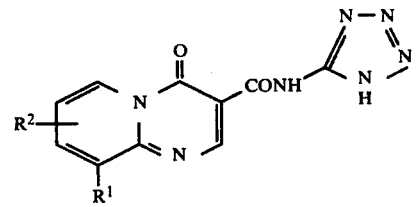

wherein $R^1$ and $R^2$ which may be the same or different are each hydrogen, halogen, (lower)alkyl, (lower)alkenyl, (lower)alkynyl, (lower)alkoxy, $CF_3$, hydroxy, (lower)alkylthio, amino, nitro, (lower)alkylamino, di(lower)alkylamino, carboxyl, phenyl, or (lower)alkylsulfinyl, or a pharmaceutically acceptable salt thereof, with the proviso that when both $R^1$ and $R^2$ are tertiary alkyl or tertiary alkoxy groups, they are located on non-adjacent positions.

4. A compound of claim 3 wherein $R^1$ and $R^2$ are each independently hydrogen, (lower)alkyl, (lower)alkenyl, (lower)alkoxy, hydroxy, (lower)alkylthio, halogen, $CF_3$, or amino.

5. A compound of the formula

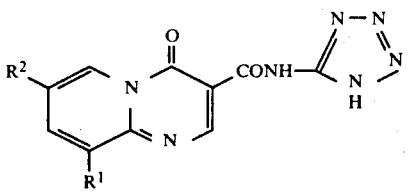

wherein $R^1$ and $R^2$ which may be the same or different are each hydrogen, halogen, (lower)alkyl, (lower)alkenyl, (lower)alkynyl, (lower)alkoxy, $CF_3$, hydroxy, (lower)alkylthio, amino, nitro, (lower)alkylamino, di(lower)alkylamino, carboxyl, phenyl, or (lower)alkylsulfinyl, or a pharmaceutically acceptable salt thereof.

6. A compound of claim 5 wherein $R^1$ and $R^2$ are each independently hydrogen, (lower)alkyl, (lower)alkenyl, (lower)alkoxy, hydroxy, (lower)alkylthio, halogen, $CF_3$, or amino.

7. The compound of claim 5 named 7,9-dimethyl-4-oxo-4H-pyrido[1,2-a]pyrimidine-3-N-(1H-tetrazol-5-yl)carboxamide, or a pharmaceutically acceptable salt thereof.

8. A compound of the formula

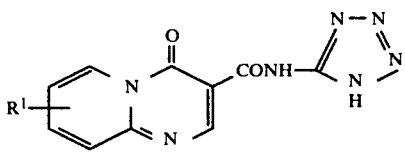

wherein $R^1$ is hydrogen, halogen, (lower)alkyl, (lower)alkenyl, (lower)alkynyl, (lower)alkoxy, $CF_3$, hydroxy, (lower)alkylthio, amino, nitro, (lower)alkylamino, di(lower)alkylamino, carboxyl, phenyl, or (lower)alkylsulfinyl, or a pharmaceutically acceptable salt thereof.

9. A compound of claim 8 wherein $R^1$ is hydrogen, (lower)alkyl, (lower)alkenyl, (lower)alkoxy, hydroxy, (lower)alkylthio, halogen, $CF_3$, or amino.

10. The compound of claim 8 named 8-methyl-4-oxo-4H-pyrido[1,2-a]pyrimidine-3-N-(1H-tetrazol-5-yl)carboxamide, or a pharmaceutically acceptable salt thereof.

11. A compound of the formula

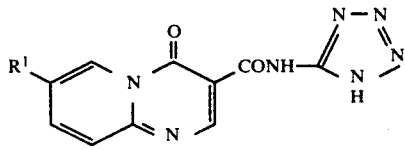

wherein $R^1$ is hydrogen, halogen, (lower)alkyl, (lower)alkenyl, (lower)alkynyl, (lower)alkoxy, $CF_3$, hydroxy, (lower)alkylthio, amino, nitro, (lower)alkylamino, di(lower)alkylamino, carboxyl, phenyl, or (lower)alkylsulfinyl, or a pharmaceutically acceptable salt thereof.

12. A compound of claim 11 wherein $R^1$ is hydrogen, (lower)alkyl, (lower)alkenyl, (lower)alkoxy, hydroxy, (lower)alkylthio, halogen, $CF_3$, or amino.

13. The compound of claim 11 named 7-methyl-4-oxo-4H-pyrido[1,2-a]pyrimidine-3-N-(1H-tetrazol-5-yl)carboxamide, or a pharmaceutically acceptable salt thereof.

14. The compound of claim 11 named 7-ethyl-4-oxo-4H-pyrido-[1,2-a]pyrimidine-3-N-(1H-tetrazol-5-yl)carboxamide, or a pharmaceutically acceptable salt thereof.

15. The compound of claim 11 named 7-n-butyl-4-oxo-4H-pyrido-[1,2-a]pyrimidine-3-N-(1H-tetrazol-5-yl)carboxamide, or a pharmaceutically acceptable salt thereof.

16. The compound of claim 11 named 7-phenyl-4-oxo-4H-pyrido-[1,2-a]pyrimidine-3-N-(1H-tetrazol-5-yl)carboxamide, or a pharmaceutically acceptable salt thereof.

17. A compound of the formula

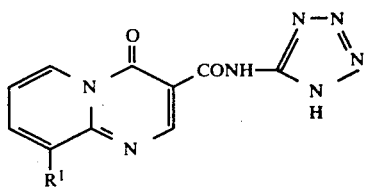

wherein $R^1$ is hydrogen, halogen, (lower)alkyl, (lower)alkenyl, (lower)alkynyl, (lower)alkoxy, $CF_3$, hydroxy, (lower)alkylthio, amino, nitro, (lower)alkylamino, di(lower)alkylamino, carboxyl, phenyl, or (lower)alkylsulfinyl, or a pharmaceutically acceptable salt thereof.

18. A compound of claim 17 wherein $R^1$ is hydrogen, (lower)alkyl, (lower)alkenyl, (lower)alkoxy, hydroxy, (lower)alkylthio, halogen, $CF_3$, or amino.

19. The compound of claim 17 named 9-methyl-4-oxo-4H-pyrido[1,2-a]pyrimidine-3-N-(1H-tetrazol-5-yl)carboxamide, or a pharmaceutically acceptable salt thereof.

20. The sodium salt of the compound of claim 19.

21. The potassium salt of the compound of claim 19.

22. The compound of claim 17 named 9-ethyl-4-oxo-4H-pyrido[1,2-a]pyrimidine-3-N-(1H-tetrazol-5-yl)carboxamide, or a pharmaceutically acceptable salt thereof.

23. The sodium salt of the compound of claim 22.

24. The potassium salt of the compound of claim 22.

25. The compound of claim 17 named 4-oxo-4H-pyrido[1,2-a]-pyrimidine-3-N-(1H-tetrazol-5-yl)carboxamide, or a pharmaceutically acceptable salt thereof.

26. The sodium salt of the compound of claim 25.

27. The potassium salt of the compound of claim 25.

* * * * *